(12) United States Patent
Bacon (10) Patent No.: US 6,422,234 B1
(45) Date of Patent: Jul. 23, 2002

(54) AEROSOL DISPENSING DEVICE

(76) Inventor: Raymond John Bacon, The Dower House, Aldsworth, Emsworth, Hampshire (GB), PO10 8OT ( * ) Notice: Subject to any disclaimer, the term of this patent is extended or adjusted under 35 U.S.C. 154(b) by 0 days.

(21) Appl. No.: 09/381,106

(22) PCT Filed: Mar. 16, 1998

(86) PCT No.: PCT/GB98/00770

§ 371 (c)(1),
(2), (4) Date: Sep. 15, 1999

(87) PCT Pub. No.: WO98/41254

PCT Pub. Date: Sep. 24, 1998

(30) Foreign Application Priority Data

Mar. 19, 1997 (GB) .............................................. 9705657

(51) Int. Cl.$^7$ ............................................. A61M 11/00
(52) U.S. Cl. .............................. 128/200.14; 128/200.23
(58) Field of Search ............................... 239/337, 576; 222/402.1, 494, 528; 128/200.14, 200.23, 203.12

(56) References Cited

U.S. PATENT DOCUMENTS

| | | | | |
|---|---|---|---|---|
| 2,773,631 A | * | 12/1956 | Bryant | 222/528 |
| 2,974,835 A | * | 3/1961 | Herbrick | 222/528 |
| 3,181,743 A | * | 5/1965 | Libit et al. | 222/528 |
| 3,187,748 A | | 6/1965 | Mitchell et al. | 128/200.23 |
| 3,294,293 A | * | 12/1966 | Johns | 222/528 |
| 3,395,838 A | * | 8/1968 | Beres et al. | 222/528 |
| 3,439,846 A | * | 4/1969 | Evras | 222/494 |
| 3,926,339 A | * | 12/1975 | Openchowski | 222/528 |
| 3,926,347 A | * | 12/1975 | Low et al. | 222/528 |
| 4,085,886 A | | 4/1978 | Nishioka | 229/62.5 |
| 4,109,836 A | * | 8/1978 | Falarde | 222/494 |
| 4,354,660 A | | 10/1982 | Stupar et al. | 251/4 |
| 4,414,972 A | * | 11/1983 | Young et al. | 128/200.23 |
| 4,570,898 A | | 2/1986 | Staeubli | 251/4 |
| 4,863,379 A | | 9/1989 | Timerdahl et al. | 433/28 |
| 5,042,526 A | | 8/1991 | Kulakoff | 137/451 |
| 5,370,279 A | | 12/1994 | Tardif | 222/214 |
| 5,667,142 A | * | 9/1997 | Newman | 239/576 |
| 5,707,038 A | | 1/1998 | Cocatre-Zilgien | 251/4 |

FOREIGN PATENT DOCUMENTS

| | | |
|---|---|---|
| FR | 2471535 | 12/1980 |
| FR | 2483262 | 5/1981 |
| GB | 1012565 | 12/1965 |

* cited by examiner

*Primary Examiner*—Aaron J. Lewis
(74) *Attorney, Agent, or Firm*—Ware, Fressola, Van Der Sluys & Adolphson LLP

(57) ABSTRACT

The dispenser (1) is for a medicament in an aerosol container (2), which is mounted in a body (3), within a sleeve (4) in a manner allowing air flow to pass the container, with the aerosol outlet tube (5) received in a socket (6) in a block (7) upstanding from the floor (8) of the body. The container is of the type which dispenses a measured dose on depression of the tube towards the container's body (9). The tube (5) is a gas tight seal in the socket (6). The block has a polyethylene tube (11) adhered into a side opening (12) of the block, in communication with the socket (6). The tube has a pair (13, 14) of kinks in it. Its end opposite from the block is adhered into a piston (15) at a throughbore (16). The piston is housed in a cylinder (17) formed in the body (3). To the outside of the cylinder is clipped an extension (18) of the body, having a mouthpiece (19) with an inhalation orifice (20). The arrangement provides an enlargement (21) in the bore (22) of the cylinder (17). The enlargement steps down in diameter to that of the (non-circular) mouthpiece, providing an abutment for a spring (23) acting on the piston and urging it in the direction of the block. Normally the tube is kinked (13, 14) by the action of the spring to such extent that it is obturated and acts as a valve (24). Thus when a dose is released into the socket (6), it is contained by the valve (24). On inhalation through the mouthpiece, the piston is drawn towards the mouthpiece against the action of the spring by the reduced pressure in the mouthpiece.

28 Claims, 7 Drawing Sheets

AEROSOL DISPENSING DEVICE

The present invention relates to a dispenser, particularly though not exclusively for dispensing aerosol or powder borne medicaments.

TECHNICAL FIELD

As used herein, "kinking" in respect of a tube means bending the tube to such extent that it collapses on itself, closing its internal passage.

BACKGROUND OF INVENTION

It is well known to administer medicines, for instance for asthma, from a dispenser adapted to provide a metered dose under gas pressure. For satisfactory administration, the patient should inhale the medicine into his/her lungs. This is eased if the dispensing is in phase with the patient's inhalation. Various dispensers exist which are actuated by the act of inhalation.

A difficulty with breath actuated dispensing is that the force available from the act of inhalation is very small, which renders simple, reliable actuation difficult. Generally the dispenser is cocked by the Application of a much greater force than can be achieved by inhalation, and the inhalation force is used to release the dose. This calls for a mechanism with several parts.

In my earlier patent U.S. Pat. No. 2,233,236, I described an aerosol medicament dispensing device in which a metered dose is received into a storage chamber and released therefrom by a breath actuated valve.

Further in another earlier application No. PCT/GB91/02118—WO 92/09323, I have proposed another aerosol medicament dispensing device in which a preload for dispensing from the aerosol is applied and resisted by pneumatic force. The pneumatic force is released by a breath actuated valve.

SUMMARY OF INVENTION

The object of my present invention is to provide a simpler alternative to my earlier dispensers, by providing a simple breath actuatable valve which can be incorporated therein.

According to the invention there is provided a valve comprising:

- a valve inlet,
- a valve outlet,
- a flexible tube extending between the inlet and the outlet, the tube having a movable portion which is movable between closed position in which the tube is kinked for closure of the valve and an open position in which the tube is un-kinked for opening of the valve and
- a movable member for moving the movable portion of the tube to control the kinking of the tube.

Whilst in some embodiments the unkinking of tube will involve at least partial straightening of it, it should be noted that the flexible tube will in most cases allow flow whilst still curved but not kinked.

The tube itself may be a length of plastics material tube. Preferably it is permanently shaped to predetermine the position of the obturating kink(s).

In certain embodiments, the tube has a single kink when the movable member and the movable portion of the tube are in their closed position, the tube then preferably having a V or L configuration. In other embodiments, the tube has a pair of kinks when closed, the tube then preferably having a Y, M or Z configuration.

The movable portion of the tube can be an end portion of the tube, connected to or providing the inlet or the outlet of the valve, in which case the end portion of the tube can be movable axially to kink and un-kink the tube, i.e. to close and open the valve, or the end portion of the tube car be movable angularly to kink and un-kink the tube.

Alternatively the movable portion of the tube can be a middle portion of the tube, between end portions connected to or providing the inlet and the outlet of the valve.

Whilst it can be envisaged that the valve will be a normally open valve, usually it will be normally closed, a spring being provided to urge the movable member to its closed position.

In particularly preferred embodiments, the valve is breath actuatable, the movable member being a vane movable by inhalation or exhalation. The vane can be a piston or a pivoted flap.

Thus the invention also provides a dispenser for a gaseous, gas borne or droplet substance, the dispenser including a valve of the invention, and further comprising:

- a body including a mouthpiece with an inhalation/insufflation orifice at its end and
- a junction for a source of gas or evaporable liquid comprising or containing the said substance, and wherein:

- the vane is movably mounted in the body for movement by the act of inhalation from a rest position towards the orifice—or at least in the direction of air flow through the dispenser—and
- the valve is connected to the junction for controlling the said gas or liquid with the valve inlet being at the junction, the flexible tube extending from the junction for receiving the said gas or liquid and connected at the outlet end to the breath actuatable vane for movement therewith, the tube being kinked to an obturating extent when the vane is in its rest position and un-kinked when the vane is moved on inhalation for release of the gas or liquid.

Whilst it is envisaged that the vane may be a diaphragm or pivoted flap, in the preferred embodiments, the vane is a piston. The vane may be inherently resilient for biasing to the rest position or may be urged there by gravity; however in the preferred embodiments, a spring is included to urge the piston to the rest position.

Preferably, the vane is a piston slidably mounted in a bore in the body at or adjacent the mouthpiece. Usually, the body and/or the piston will be provided with an air bypass to enable air to be inhaled to bypass the piston when it has moved the tube to its un-kinked, open position. The bypass can be a series of notches in a skirt of the piston and an enlargement in the bore, the bypass opening when the notches move into register with the enlargement.

In accordance with another feature, the piston is provided with a manually actuatable member extending through a wall of its bore and the piston and its bore are provided with a notch and detent mechanism for holding the piston in either or both of its open and closed positions, whereby the piston can be manually moved to and held in its position holding the tube in its kinked, closed and/or to its un-kinked open position by engagement of the notch and detent mechanism. Alternatively, a manually actuatable member may be provided merely for holding the piston in its open position with the tube un-kinked and open for purging discharge from the said source.

Where a spring is provided for normally closing the valve, it can be a compression spring biasing the piston inwardly of the mouthpiece, the spring acting between the piston and an abutment in the body. Alternatively, the spring can be a tension spring biasing the piston inwardly of the mouthpiece, the piston and a formation in the body being adapted to connect to the spring for its biasing of the piston.

In one embodiment, a dispenser is provided for use with a source of the substance in pressurised gaseous or liquid form of the type which releases a dose on depression of an outlet tube of the source, wherein:

the body is generally L-shaped,
one limb of the L is a sleeve for accommodating the source of gas or evaporable liquid,
the other limb terminates as the mouthpiece,
a block:
   is provided integrally with and internally of the body in line with the one limb,
   has a socket for receiving an outlet tube of the source and
   is the junction to the valve with the socket in communication with the valve tube, and
the piston is the outlet from the valve and has the valve tube in communication with a throughbore in the piston,
the arrangement being such that depression of the source in the one limb releases a dose of the said substance into the valve tube for release on valve opening by inhalation.

In this embodiment, the block preferably has a lateral communication with the valve tube and the latter has a Z configuration when kinked and closed.

In another embodiment, a dispenser is provided for use with a source of the substance in pressurised gaseous or liquid form of the type which releases a dose on depression of an outlet tube of the source, wherein:

the body is generally L-shaped,
one limb of the L is a sleeve for accommodating and captivating the source of gas or evaporable liquid,
the other limb terminates as the mouthpiece,
a block:
   is provided movably in the body in line with the one limb,
   has a socket for receiving an outlet tube of the source inside the body and an actuation button outside the body and
   is the junction to the valve with the socket in communication with the valve tube, and
the piston is the outlet from the valve and has the valve tube in communication with a throughbore in the piston,
the arrangement being such that depression of the button towards the body releases a dose of the said substance into the valve tube for release on valve opening by inhalation.

In this embodiment, the block preferably has an axial communication with the valve tube and the latter has an L configuration when kinked and closed.

In yet another embodiment, a dispenser is provided for a gaseous, gas borne or droplet substance, the dispenser including a valve of the invention and further comprising:

a body including a mouthpiece with an inhalation/insufflation orifice at its distal end,
a source of the substance in pressurised gaseous or liquid form of the type having a container and a depressable outlet tube which releases a dose on depression towards the container and
depression means for releasing a dose, the depression means including:
   a depression spring arranged to act on the source for releasing a dose,
   a pneumatic actuator for resisting the action of the spring when a chamber of the actuator is closed,
   a port opening into the chamber,
   means for compressing the spring to cock the dispenser and
   non-return means for allowing air to escape from the chamber as it is compressed for cocking,
and wherein:
   the vane is movably mounted in the body for movement from a rest position towards the orifice by the act of inhalation and
   the valve is arranged for controlling the port into the chamber, the port being the outlet from the valve, the flexible tube being secured at its inlet end to the breath actuatable vane for movement therewith, the tube being kinked to an obturating extent when the vane is in its rest position and unkinked when the vane is moved towards the orifice on inhalation for release of the contents of the container by allowing air to enter the chamber and the spring to act to release the dose.

In this embodiment, the vane is preferably a flap pivotably mounted in the body and the spring is a torsion spring acting about the pivot of the flap in body.

Whilst the dispensers may find use for continuous dispensing, normally they will be used for dispensing metered doses. These may be released by the source of gas or liquid in measured doses. However it is envisaged that the source may be arranged to release into a space at least partially limited by an obturating kink to measure the dose.

BRIEF DESCRIPTION OF THE DRAWINGS

To help understanding of the invention, two specific embodiments thereof will now be described by way of example and with reference to the accompanying drawings, in which.

BEST MODE FOR CARRYING OUT THE INVENTION

Figure 1:
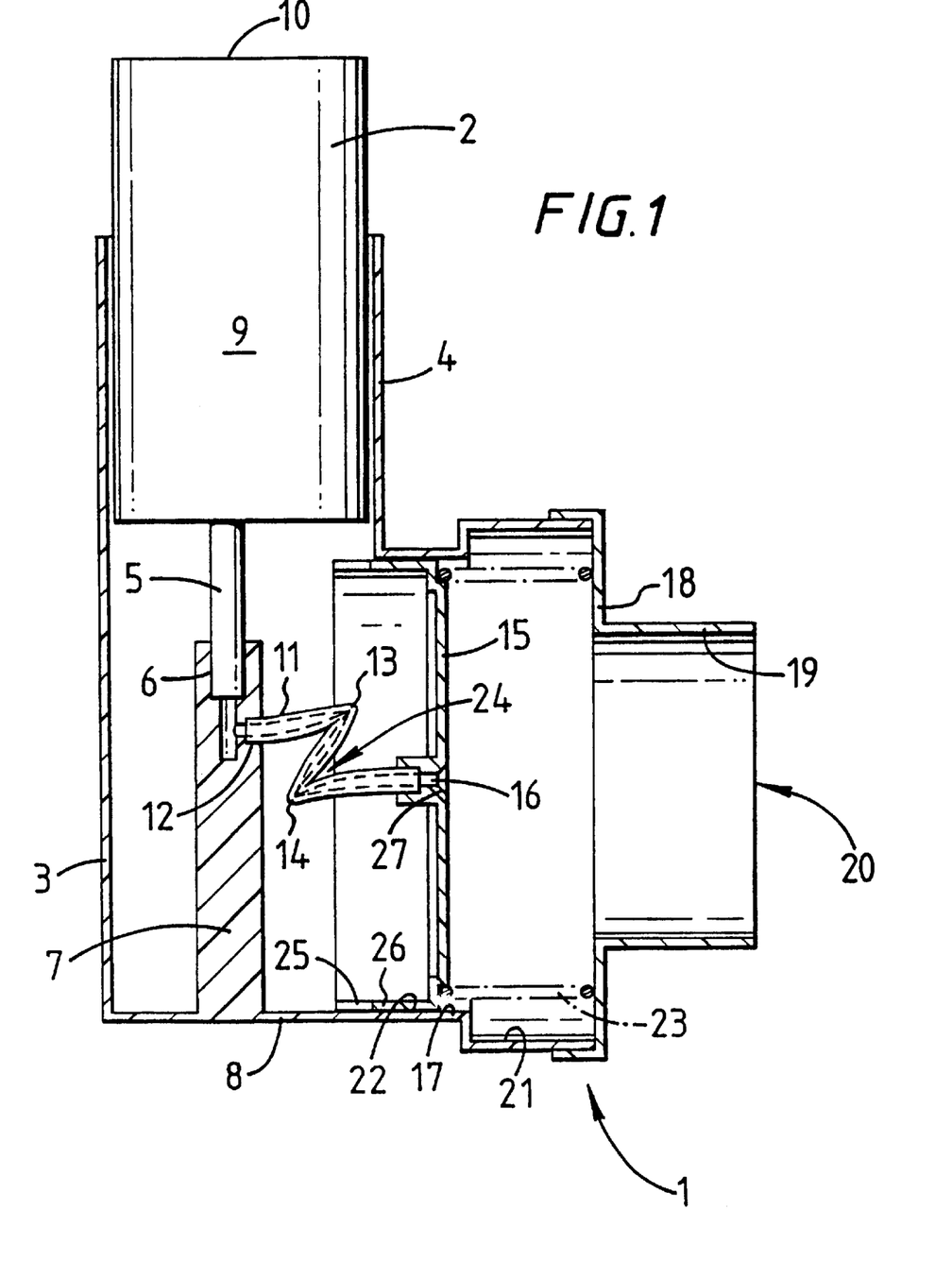
FIG. 1 is a cross-sectional side view of a dispenser according to the invention, with its piston and kinked tube at rest in its obturating position.
Figure 2:
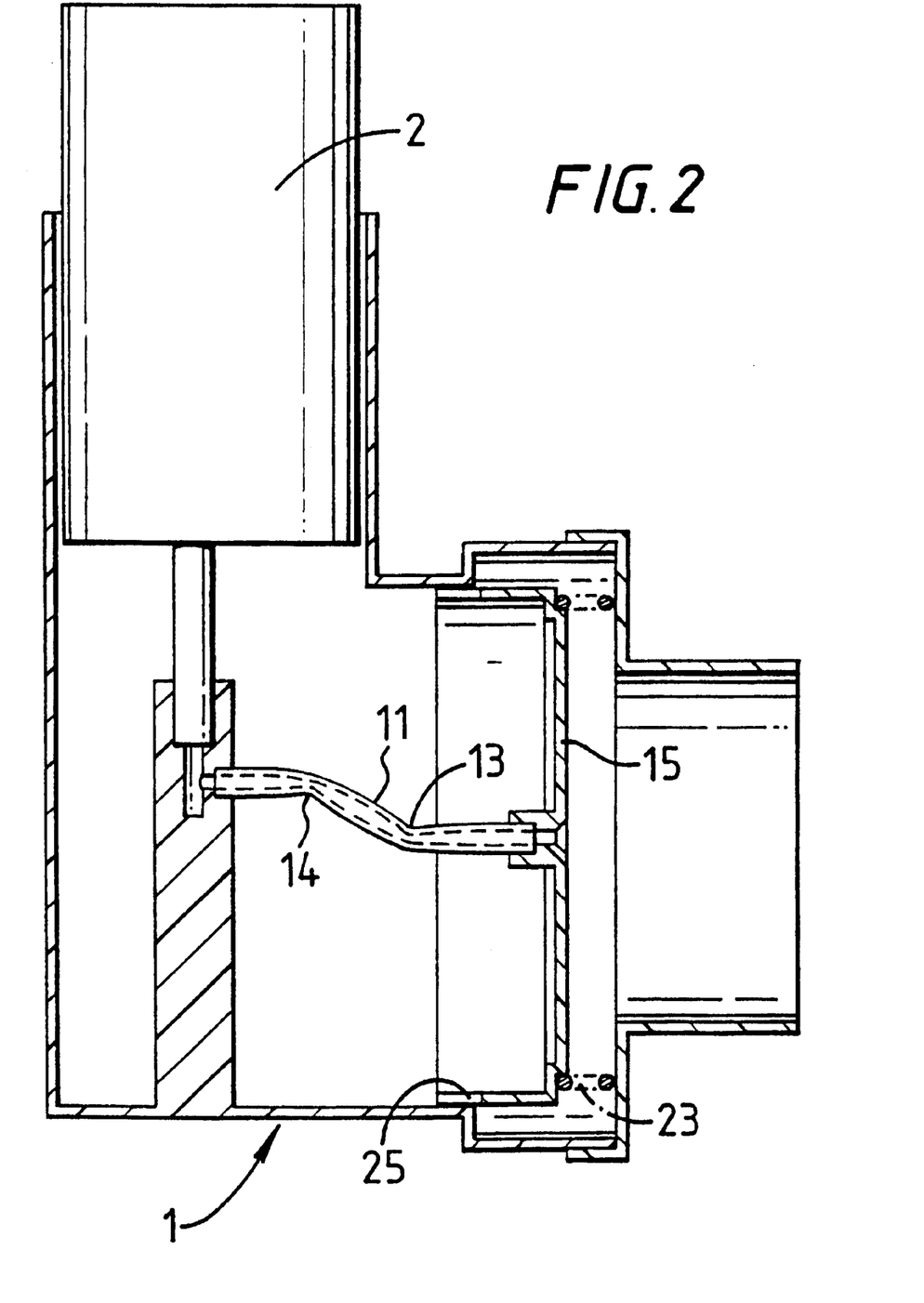
FIG. 2 is a similar view with the dispenser with the piston moved forwards to open the tube.

Turning first to FIGS. 1 and 2, the dispenser 1 thereshown is for a medicament contained in a pressurised aerosol canister or container 2 and dissolved/suspended in the aerosol propellant. The container is mounted in an injection moulded, polypropylene body 3 of the dispenser, within a sleeve 4 in a manner allowing air flow to pass the container, with the aerosol outlet tube 5 received in a socket 6 in a block 7 upstanding from the floor 8 of the body. The container is of the type which dispenses a measured dose on depression of the tube towards the container's body 9. In practice, the depression is achieved by pressure between the end 10 of the container and the floor 8. The tube 5 is a gas tight seal in the socket 6, so that a released dose is retained in the dispenser, by the valve of the invention which will now be described.

The block has a polyethylene tube 11 adhered into a side opening 12 of the block, in communication with the socket 6. The tube has a pair 13,14 of kinks in it. Its end opposite from the block is adhered into a piston 15 at a throughbore 16. The piston is housed in a cylinder 17 formed in the body 3. To the outside of the cylinder is clipped an extension 18 of the body, having a mouthpiece 19 with an inhalation orifice 20. The arrangement provides an enlargement 21 in the bore 22 of the cylinder 17. The enlargement steps down in diameter to that of the (non-circular) mouthpiece, providing an abutment for a spring 23 acting on the piston and urging it in the direction of the block.

Normally the tube is kinked 13,14 by the action of the spring to such extent that it is obturated and acts as a valve 24. Thus when a dose is released into the socket 6, it is contained by the valve 24. On inhalation through the mouthpiece, the piston is drawn towards the mouthpiece against the action of the spring by the reduced pressure in the mouthpiece. This movement to the position shown in FIG. 2 is limited by the spring becoming coil-bound. Air can then flow around the piston via notches 25 in a skirt 26 of the piston at the cylinder's step in diameter. When the piston is in this position, the tube has straightened sufficiently to release the obturation at the kinks, so that the dose can flow through the throughbore 16 which has a mouth 27 shaped for aeorsol dispersion. Thus the dose is released for inhalation by the patient.

Figure 3:
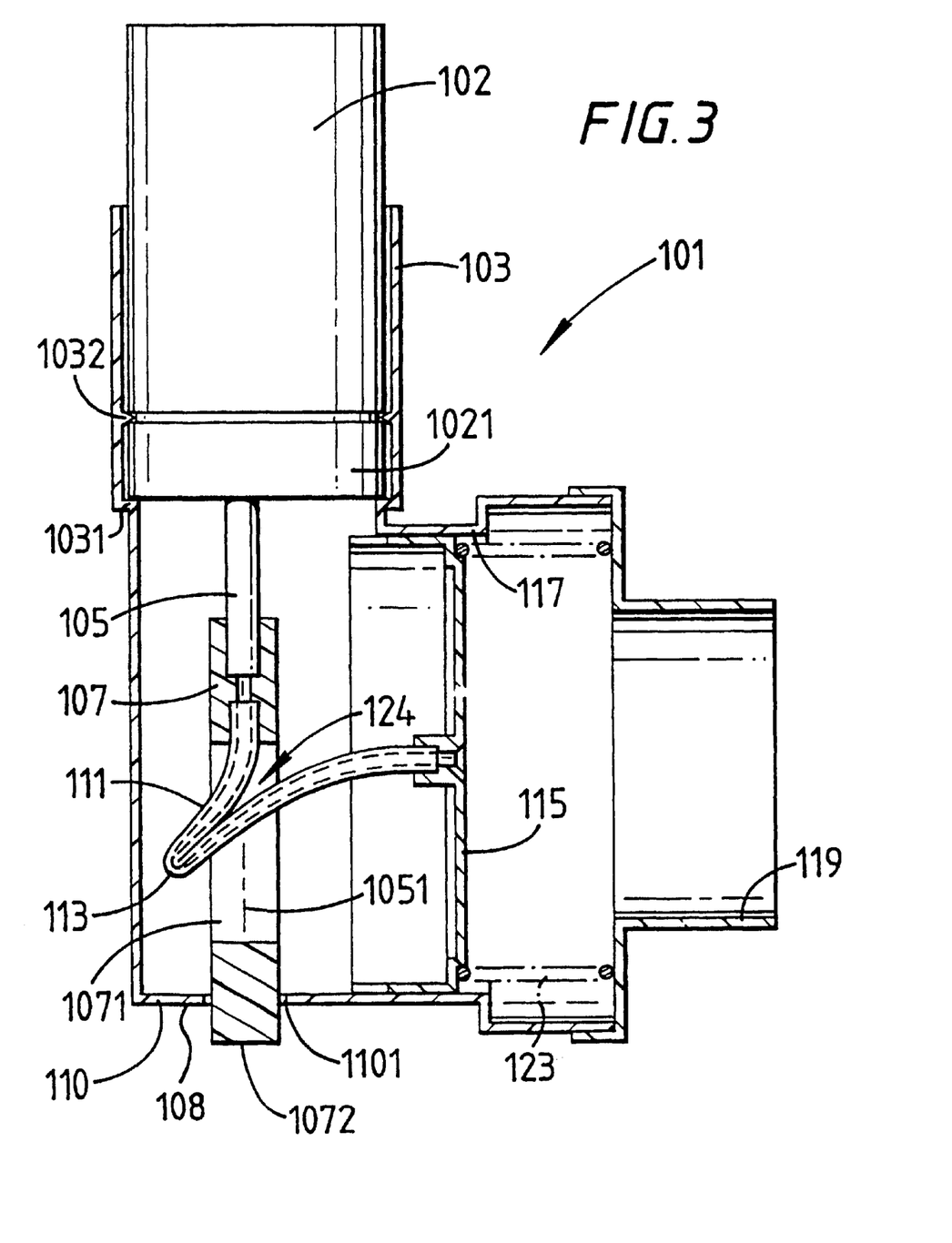
FIG. 3 is a cross-sectional side view of another dispenser according to the invention, with its piston and kinked tube at rest in its obturating position.
Figure 4:
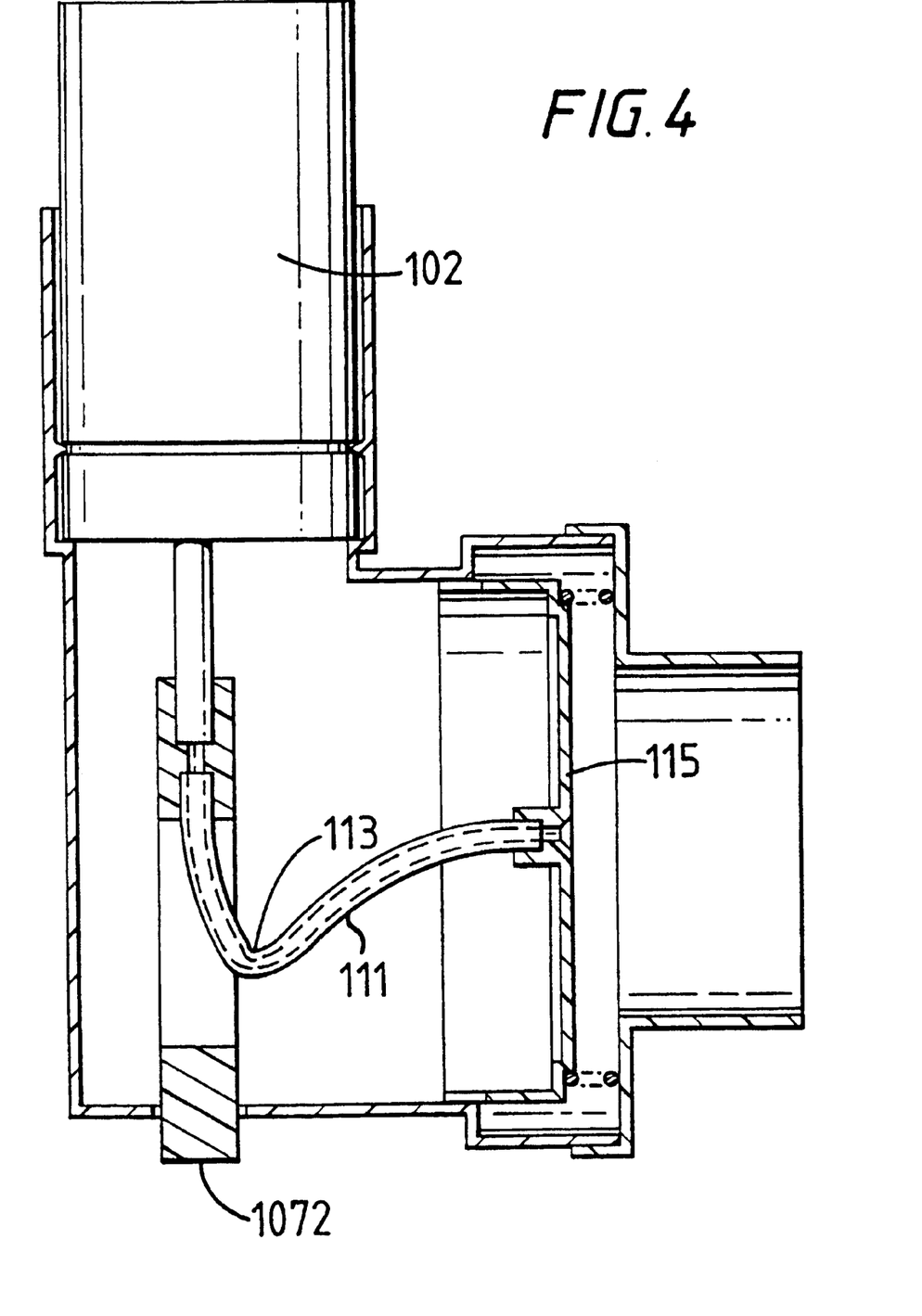
FIG. 4 is a similar view with the dispenser of FIG. 3 with its piston moved forwards to open its tube.

Turning now to FIGS. 3 & 4, the dispenser 101 thereshown has its aerosol container 102 located in a sleeve 103 of the dispenser body at an internal step 1031, against which the rolled on cap 1021 of the container abuts. Resilient studs 1032, over which the cap rides on insertion of the container into the sleeve, spring out behind the cap to captivate the container. The container's outlet tube 105 has a polyethylene tube 111 connected to it by a movable actuation block 107, which is bifurcated in its middle section with the tube passing through the bifurcation 1071. The remote end 1072 of the actuation block is in the form of a button extends through an aperture 1101 in the floor 108 of the body.

The piston 115, cylinder 117, spring 123 and mouthpiece 119 of the dispenser 101 are similar to those of the dispenser 1 and will not be described in detail.

The tube 111 is kinked 113 and of such length that when the piston is at rest, the kink 113 is on the opposite side of the axis 1051 of the outlet tube and closes the valve 124 of which it is the operative part. On inhalation the piston moves the tube sufficiently for the kink to unseal.

For use of the device, the button 1072 is pressed inwards. The container's valve is an ordinary release valve, as opposed to a metering valve and the outlet tube 105 and the polyethylene tube 111 down to the kink fills with released aerosol liquid. The button is then released so that the volume of the dose is determined by the volume of the tubes 105,111 to the kink. Then on inhalation, the dose is released in the manner of the first embodiment.

Figure 5:
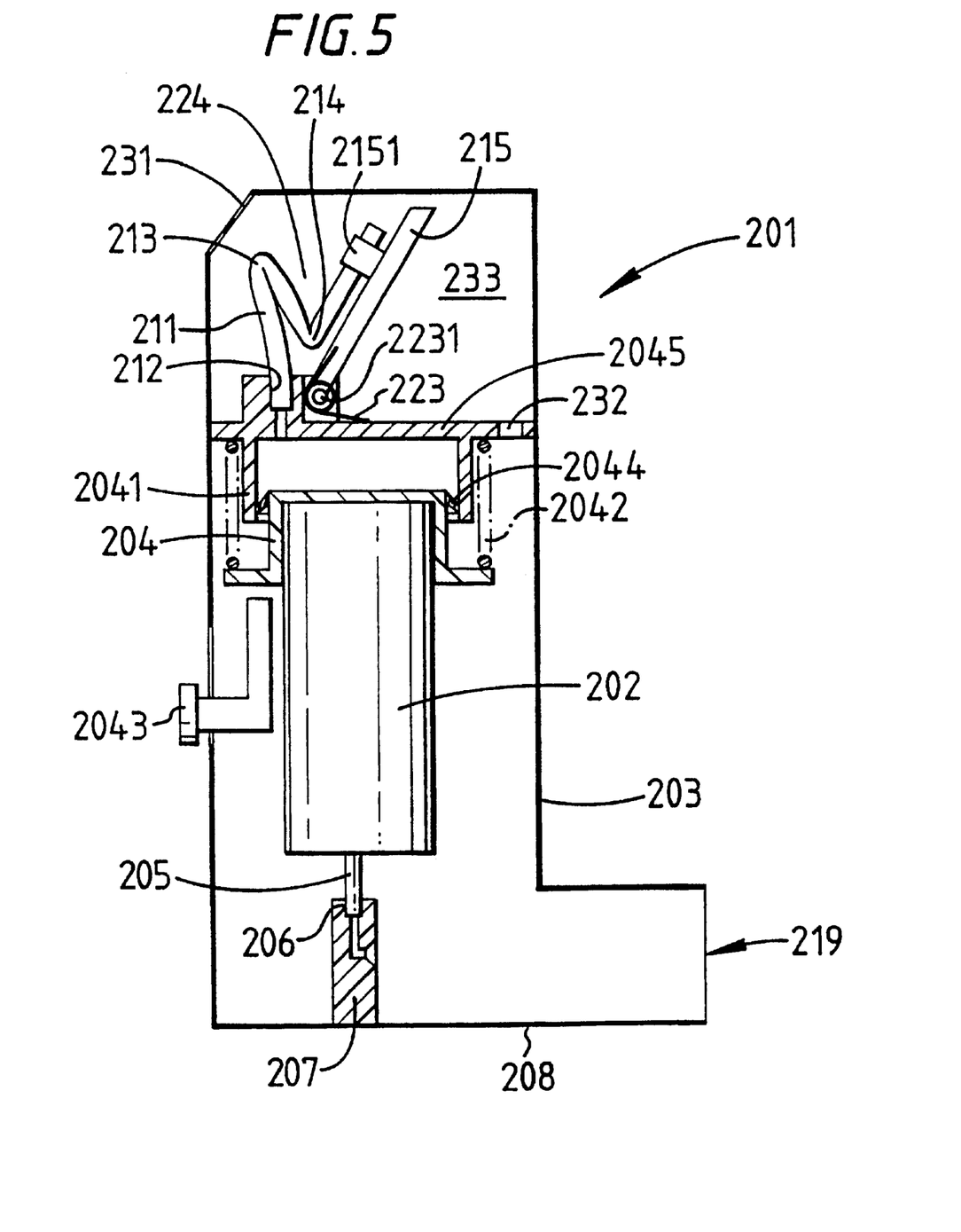
FIG. 5 is a similar view of a further dispenser according to the invention.

Turning now to FIG. 5, the dispenser 201 thereshown includes an aerosol medicament container 202 in a body 203. The aerosol outlet tube 205 is received in a socket 206 in block 207 upstanding from the floor 208 of the body. A mouthpiece 219 is provided adjacent the block 207. The opposite end of the container is received in a short sleeve/piston 204, which is arranged as a piston in a second sleeve/cylinder 2041. The latter is moulded integrally with the body 203. A spring 2042 urges the piston out of the cylinder, whilst a slide knob 2043 is provided for urging the, piston inwards. The piston is moulded with an integral lip 2044, which allows air in the cylinder to pass out on inwards movement of the piston, but does not allow air into the cylinder under the action of the spring 2042. Thus whilst the cylinder remains closed, after cocking of the dispenser by pushing of the knob 2043 upwards, the piston 204 is pneumatically held in position until released, whereupon the action of the spring forces the container down causing movement of the outlet tube inwards of the container for dispensing of the aerosol medicament.

Pivotally mounted on the end 2045 of the cylinder 2041, is a flap 215, which is urged to its position shown in FIG. 5 by a torsion spring 223, mounted on a pivot pin 2231. A tube 211 with kinks 213,214 is adhered at one end into an opening 212 in the cylinder end 2045. The other end of the tube is clipped 2151 to the flap 215. In practice to accommodate the tube, the kink 213 may be a bend not completely obturating the tube, but with the kink 214 obturating the tube in the FIG. 5 position.

The top of the body 203 has an air inlet opening 231 and an air passage 232 is provided to connect the mouthpiece to the space 233 on the side of the flap 215 opposite from the inlet 231.

On cocking of the dispenser as described above, the kink valve 224 prevents air from entering the cylinder, despite the action of the spring 2042. On inhalation through the mouthpiece, a pressure differential is developed across the flap 215, pivoting it down against its spring 223. This movement unkinks the tube 211 sufficiently for air to pass through it which allows the spring 2042 to actuate dispensing from the container.

Figure 6:
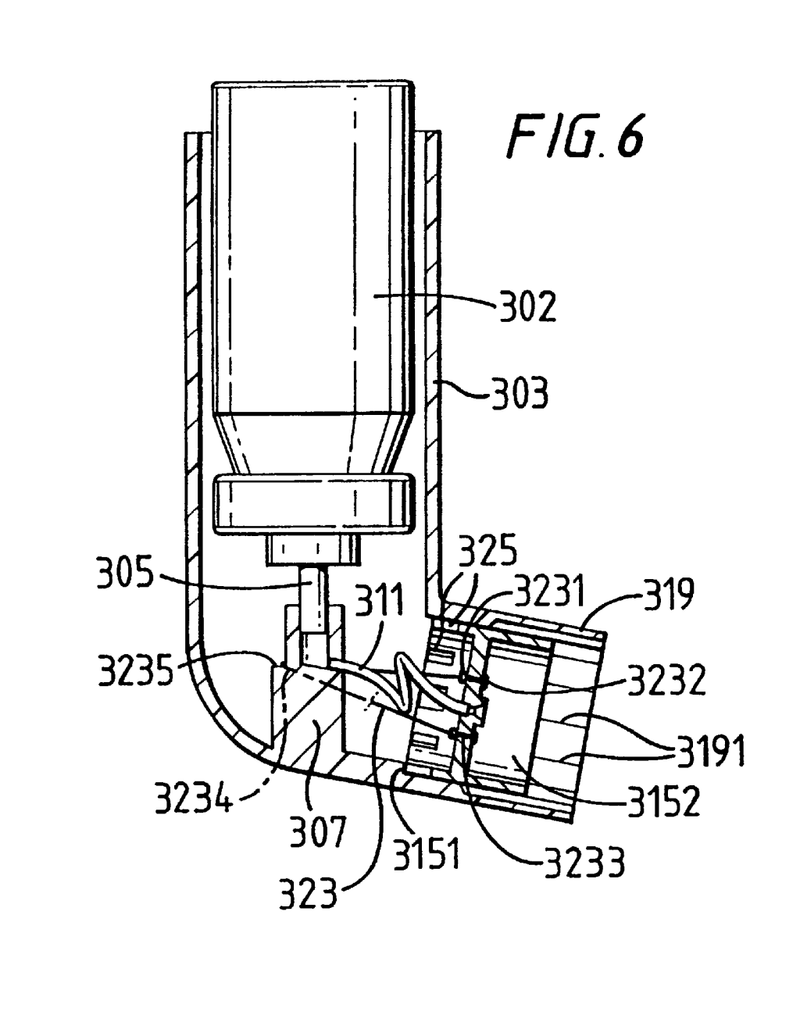
FIG. 6 is a view similar to FIG. 1 of a fourth dispenser according to the invention.

Turning now to FIG. 6, the dispenser there shown is largely similar to the dispenser of FIGS. 1 & 2. The chief difference is that the spring 323 is a tension spring of elastomeric material. It is of the type having moulded end formations 3231,3232, which enable it to be fitted by drawing outer ones 3232 through apertures 3233 in the piston 315 of the dispenser. The arrangement is such that the formations 3231,3232 close the apertures 3233. The middle portion 3234 of the spring is taken around the block 307 for the outlet tube 305 of the aerosol container 302. A step 3235 is provided for locating the spring. The latter draws the piston 315 against a stop 3151 moulded within the root of the mouthpiece 319, which is an integral moulding with the body 303 of the dispenser. With the piston against the stop, the kink tube 311 is closed in Z formation with closed kinks at the corners. Within the orifice of the mouthpiece, a series of ribs 3191 are provided for the guiding the skirt 3152 of the piston, whilst at the same time allowing an air passage around the piston enabling air to be inhaled past it when the piston has been drawn forwards to open the valve and allow air to pass into the mouthpiece via notches 325 in the inner skirt.

Although the spring is shown as an elastomeric spring, it could be replaced by a metal coil spring.

Figure 7:
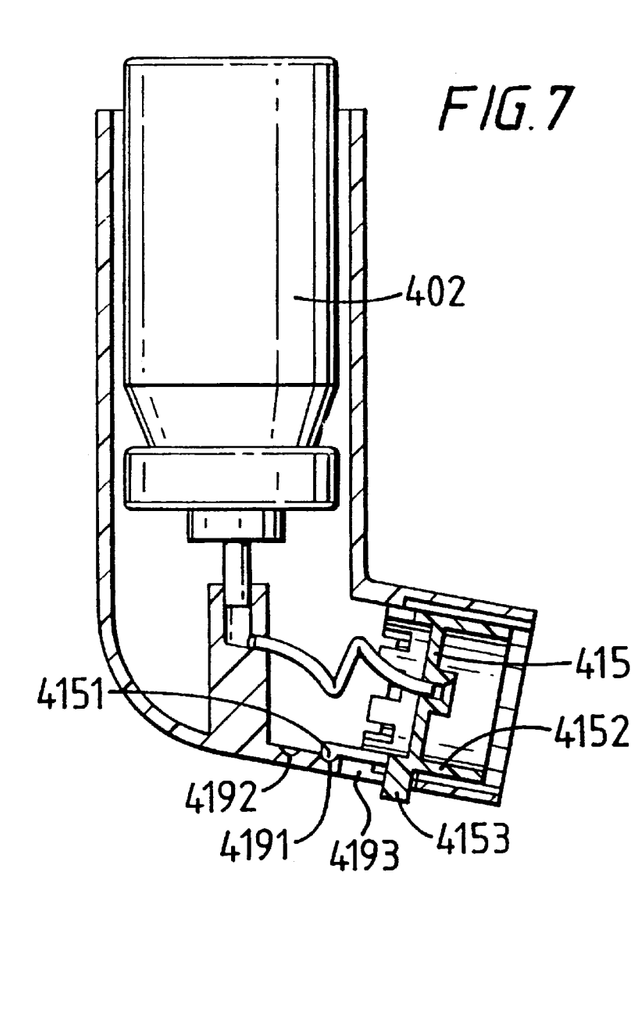
FIG. 7 is a similar view of a fifth dispenser according to the invention.

Turning on to FIG. 7, this dispenser has no spring for holding the piston back and the valve closed before inhalation. It does have a detent 4151 moulded as an inwards extension of the skirt 4152 of it piston 415. Also the skirt has attached to it a knob 4153, for manually moving the piston. The bore of the mouthpiece has two notches 4191,4192 moulded internally for co-operation with the detent. The mouthpiece also has a slot 4193 for the knob 4153. This arrangement allows the dispenser to be stored with the kink valve open and the detent engaged in the outer notch 4191. When it is to be used, the dosage mechanism in the canister 402 can be primed by depression of the canister until a dose is expelled through the piston. Then the piston is slid back by use of the knob so as to engage the detent in the inner notch 4192. This closes the valve and a dose to be inhaled can be released into the kink tube by depression of the canister 402. On inhalation, the frictional location of the piston by the detent is overcome by the inhalation, the piston moves forwards and the dose is released. For the next dose, the piston is moved back for the process to be repeated.

Figures 8, 9:
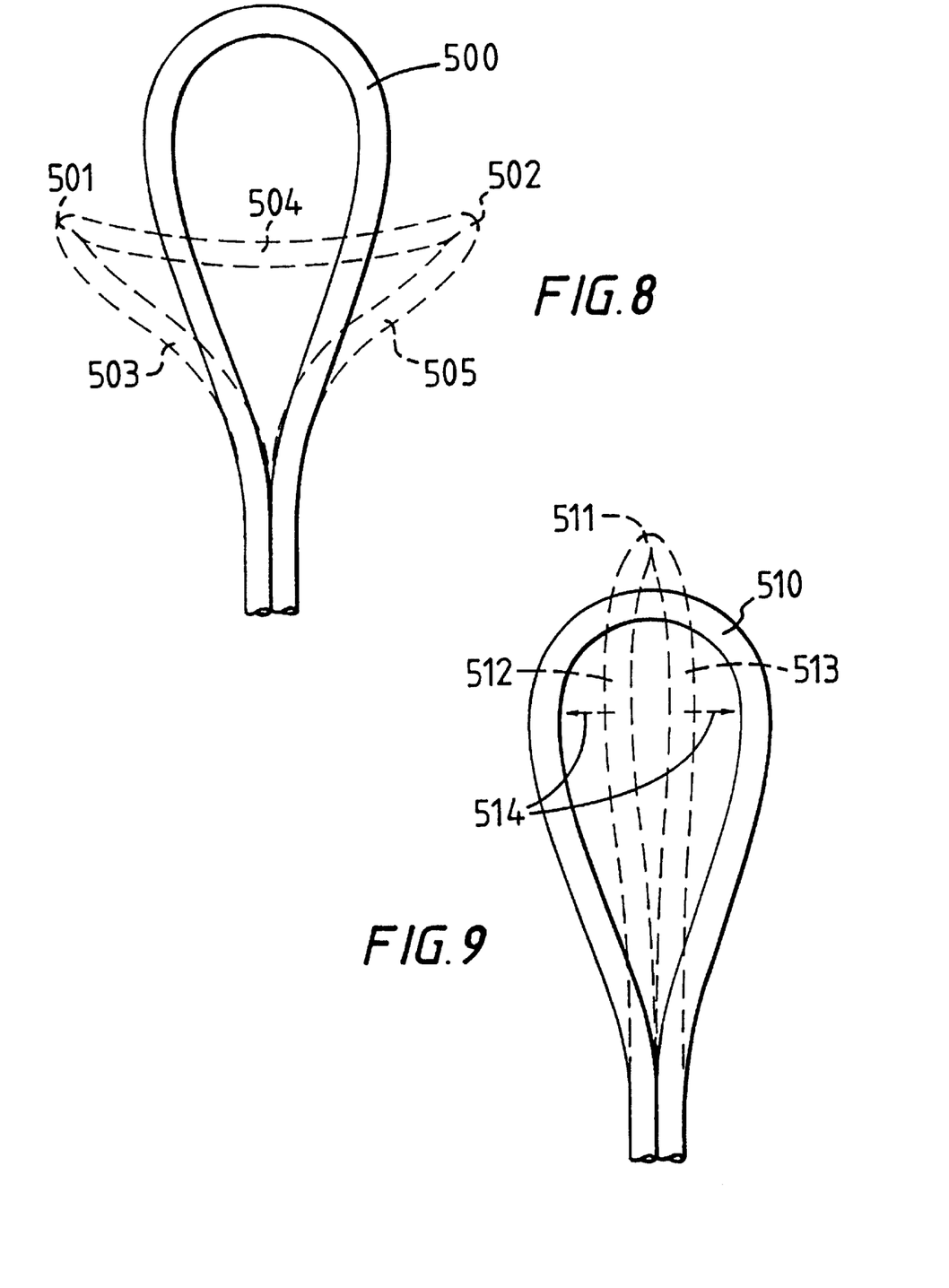
FIG. 8 is a diagrammatic view of an alternative obturation arrangement.
FIG. 9 is a similar diagrammatic view of another alternative obturation arrangement.

Lastly referring to FIGS. 8 and 9, there are shown two alternative configurations for kink valve tubes. In each, a loop of tube is shown unkinked in full lines and kinked in broken lines. FIG. 8 shows a Y or M configuration, in which action on the loop 500 from the end creates two kinks 501,502. Where the material of the tube is at least slightly elastic, the unkinked shape is recovered without assistance due to bending in the three sections 503,504,505 into which the tube is divided by the kinks. In FIG. 9, action on the loop 510 from the sides results in one kink 511. Since the two sections 512,513 of the tube are not under bending, a restoring force in the direction of arrows 514 is required to unkink the tube.

The invention is not intended to be restricted to the details of the above described embodiments. For instance, the two tubes 105 and 111 can be integrally formed. The dispenser may be a dry powder dispenser either having means for dispensing a pre-metered dose of powder or metering a dose of powder, either of which is fluidised for inhalation by a dose of gas released by a kink valve operated by a piston or other vane in the manner of the described embodiments. It should also be specifically noted that the invention can be used in nasal insufflation devices as well as mouth inhalation devices. Again it can be envisaged that a mouthpiece cap or a separate clip can be pivoted onto the end of the canister to hold it depressed immediately prior to inhalation.

What is claimed is:

1. A dispenser for a gaseous, gas borne or droplet substance, the dispenser including:
    a body having a mouthpiece connected thereto, the mouthpiece having an inhalation/insufflation orifice;
    a junction in the body for receipt of the substance; and
    a breath actuable valve, for controlling the release of said substance, comprising:
        a valve inlet connected to the junction;
        a valve outlet;
        a flexible tube extending from the junction, between the inlet and the outlet, for receiving the substance, the tube having a portion which is movable bodily between a closed position in which the tube is kinked, that is, bent to such an extent that it collapses on itself with an abrupt change in orientation of adjoining portions of said part of the tube for closure of the valve and an open position in which the tube is un-kinked for opening of the valve; and
        a movable member, for moving the movable portion of the tube to control its kinking, and being movably mounted in the body for movement by the act of inhalation from a rest position towards the orifice or at least in the direction of air flow through the dispenser;
        the tube being kinked to an obturating extent when the movable member and the bodily movable portion of the tube are in a rest position and un-kinked when the movable member and the bodily movable portion of the tube are moved on inhalation for release of the substance.

2. A dispenser as claimed in claim 1, wherein the tube has a single kink when the movable member and the movable portion of the tube are in their closed position, the tube then having a V or L configuration.

3. A dispenser as claimed in claim 1, wherein the tube has a pair of kinks when the movable member and the movable portion of the tube are in their closed position, the tube then having a Y, M or Z configuration.

4. A dispenser as claimed in claim 1, wherein the movable portion of the tube is an end portion of the tube, connected to or providing the inlet or the outlet of the valve.

5. A dispenser as claimed in claim 4, wherein the end portion of the tube is movable axially to kink and un-kink the tube.

6. A dispenser as claimed in claim 4, wherein the end portion of the tube is movable angularly to kink and un-kink the tube.

7. A dispenser as claimed in claim 1, wherein the movable portion of the tube is a middle portion of the tube, between end portions connected to or providing the inlet and the outlet of the value.

8. A dispenser as claimed in claim 1, wherein the valve is normally closed, a spring being provided to urge the movable member to its closed position.

9. A dispenser as claimed in claim 8, wherein the movable member is a piston slidably mounted in a bore in the body at or adjacent the mouthpiece.

10. A dispenser as claimed in claim 9, wherein the body and/or the piston is provided with an air bypass to enable air to be inhaled to bypass the piston when it has moved the tube to its un-kinked, open position.

11. A dispenser as claimed in claim 10, wherein the bypass is a series of notches in a skirt of the piston and an enlargement in the bore, the bypass opening when the notches move into register with the enlargement.

12. A dispenser as claimed in claim 9, wherein:
    the piston is provided with a manually actuatable member extending through a wall of its bore and
    the piston and its bore are provided with a notch and detent mechanism for holding the piston in either or both of its open and closed positions,
    whereby the piston can be manually moved to and held in its position holding the tube in its kinked, closed and/or to its un-kinked open position by engagement of the notch and detent mechanism.

13. A dispenser as claimed in claim 9, wherein the piston is provided with a manually actuatable member for holding it in its open position with the tube un-kinked and open for purging discharge from the said source.

14. A dispenser as claimed in claim 9, wherein the spring is a compression spring biasing the piston inwardly of the mouthpiece, the spring acting between the piston and an abutment in the body.

15. A dispenser as claimed in claim 9, wherein the spring is a tension spring biasing the piston inwardly of the mouthpiece, the piston and a formation in the body being adapted to connect to the spring for its biasing of the piston.

16. A dispenser as claimed in claim 9 for use with a source of the substance in pressurised gaseous or liquid form of the type which releases a dose on depression of an outlet tube of the source, wherein;

the body is generally L-shaped, one limb of the L is a sleeve for accommodating the source of gas or evaporable liquid, the other limb terminates as the mouthpiece, a block:
- is provided integrally with and internally of the body in line with the one limb, has a socket for receiving an outlet tube of the source and is the junction to the valve with the socket in communication with the valve tube, and
- the piston is the outlet from the valve and has the valve tube in communication with a throughbore in the piston, the arrangement being such that depression of the source in the one limb releases a dose of the said substance into the valve tube for release on valve opening by inhalation.

17. A dispenser as claimed in claim 16, wherein the block has a lateral communication with the valve tube and the latter has a Z configuration when kinked and closed.

18. A dispenser as claimed in claim 9 for use with a source of the substance in pressurised gaseous or liquid form of the type which releases a dose on depression of an outlet tube of the source, wherein:

the body is generally L-shaped, one limb of the L is a sleeve for accommodating and captivating the source of gas or evaporable liquid, the other limb terminates as the mouthpiece, a block:
- is provided movably in the body in line with the one limb,
- has a socket for receiving an outlet tube of the source inside the body and an actuation button outside the body and
- is the junction to the valve with the socket in communication with the valve tube, and
- the piston is the outlet from the valve and has the valve tube in communication with a throughbore in the piston, the arrangement being such that depression of the button towards the body releases a dose of the said substance into the valve tube for release on valve opening by inhalation.

19. A dispenser as claimed in claim 18, wherein the block has an axial communication with the valve tube and the latter has an L configuration when kinked and closed.

20. A dispenser for a gaseous, gas borne or droplet substance, the dispenser including:

a body including a mouthpiece with an inhalation/insufflation orifice at its distal end;

a source of the substance, in the body, in pressurised gaseous or liquid form of the type having a container and a depressable outlet tube which releases a dose on depression toward the container;

depression means for releasing a dose, the depression means including:

a depression spring arranged to act on the source for releasing a dose;

a pneumatic actuator for resisting the action of the spring when a chamber of the actuator is closed;

a port opening into the chamber;

means for compressing the spring to cock the dispenser; and non-return means for allowing air to escape from the chamber as it is compressed for cocking; and a breath actuable valve, for controlling the port into the chamber, comprising:

a valve inlet;

a valve outlet, connected to the port;

a flexible tube extending between the inlet and the outlet, the tube having a portion which is movable between a closed position in which the tube is kinked for closure of the valve and an open position in which the tube in un-kinked for opening of the valve;

a movable member, movably mounted in the body and connected to the valve inlet for movement therewith, for moving the movable portion of the tube to control the kinking of the tube, the tube being kinked to an obdurating extent when the movable member is in its rest position and unkinked when the movable member is moved towards the orifice on inhalation for release of the contents of the container by allowing air to enter the chamber and the spring to act to release the dose.

21. A dispenser as claimed in claim 20, wherein the tube has a single kink when the movable member and the movable portion of the tube are in their closed position, the tube then having a V or L configuration.

22. A dispenser as claimed in claim 20, wherein the tube has a pair of kinks when the movable member and the movable portion of the tube are in their closed position, the tube then having a Y, M or Z configuration.

23. A disperser as claimed in claim 20, wherein the movable portion of the tube is an end portion of the tude, connected to or providing the inlet or the outlet of the valve.

24. A dispenser as claimed in claim 23, wherein the end portion of the tube is movable axially to kink and un-kink the tube.

25. A dispenser as claimed in claim 23, wherein the end portion of the tube is movable angularly to kink and un-kink the tube.

26. A dispenser as claimed in claim 25, wherein the movable member is a flap pivotably mounted in the body.

27. A dispenser as claimed in claim 26, wherein the spring is a torsion spring acting about the pivot of the flap in body.

28. A dispenser as claimed in claim 20, wherein the movable portion of the tube is a middle portion of the tube, between end portions connected to or providing the inlet and the outlet of the valve.

* * * * *